US011419695B2

(12) United States Patent
Kehren-Quitsdorf et al.

(10) Patent No.: US 11,419,695 B2
(45) Date of Patent: Aug. 23, 2022

(54) LIGHT INSTRUMENT FOR ILLUMINATING THE INTRAOCULAR SPACE

(71) Applicant: OERTLI-INSTRUMENTE AG, Berneck (CH)

(72) Inventors: Lisa Kehren-Quitsdorf, Arbon (CH); Lothar Knünz, Rankweil (AT); Michael Zürcher, St. Gallen (CH)

(73) Assignee: OERTLI-INSTRUMENTE AG, Berneck (CH)

( * ) Notice: Subject to any disclaimer, the term of this patent is extended or adjusted under 35 U.S.C. 154(b) by 0 days.

(21) Appl. No.: 16/875,249

(22) Filed: May 15, 2020

(65) Prior Publication Data
US 2020/0360104 A1 Nov. 19, 2020

(30) Foreign Application Priority Data
May 17, 2019 (EP) .................................... 19175168

(51) Int. Cl.
*A61B 90/30* (2016.01)
*A61B 90/20* (2016.01)
(Continued)

(52) U.S. Cl.
CPC .............. *A61B 90/30* (2016.02); *A61B 90/20* (2016.02); *A61F 9/00736* (2013.01); *A61B 3/0008* (2013.01); *A61B 2090/308* (2016.02)

(58) Field of Classification Search
CPC .............. A61B 90/30; A61B 2090/304; A61B 2090/306; A61B 2090/308; A61B 2090/309; A61B 3/008
See application file for complete search history.

(56) References Cited

U.S. PATENT DOCUMENTS 5,348,019 A * 9/1994 Sluss, Jr. ................ A61B 5/037
600/480
7,141,048 B1 * 11/2006 Charles ............... A61F 9/00736
606/4
(Continued)

FOREIGN PATENT DOCUMENTS

CH           710 150 A2     3/2016

OTHER PUBLICATIONS

European Committee for Standardization, European Standard, 2010, CEN, vol. 15752, https://www.iso.org/obp/ui/#iso:std:iso:15752:ed-2:v1:en (Year: 2010).*

(Continued)

*Primary Examiner* — Juliannan Harvey
*Assistant Examiner* — Holly Joanna Lane
(74) *Attorney, Agent, or Firm* — Sughrue Mion, PLLC

(57) ABSTRACT

A device (2) for an ophthalmological illumination system (1) comprising a light instrument (3) for illuminating the intraocular space of a human or animal eye (33) comprises a housing (4) having a proximal housing end (5), a distal housing end (6), and an opening (7) in the proximal housing end (5). The housing (4) delimits a receptacle space (8), which extends in a manner proceeding from the opening (7) in the proximal housing end (5) along a longitudinal direction (L) in the direction of the distal housing end (6). The receptacle space (8) is configured for receiving the light instrument (3) through the opening (7) in the proximal housing end (5). The housing (4) comprises at least one translucent material at least in the region (10) of the distal housing end (6).

18 Claims, 15 Drawing Sheets

(51) Int. Cl.
*A61F 9/007* (2006.01)
*A61B 3/00* (2006.01)

(56) References Cited

U.S. PATENT DOCUMENTS

| | | | |
|---|---|---|---|
| 7,428,350 B1 * | 9/2008 | Varadarajan | E21B 47/135 385/13 |
| 10,179,067 B2 * | 1/2019 | Olson | A61B 3/0008 |
| 10,238,417 B1 * | 3/2019 | Carpenter | A61B 17/32 |
| 2005/0075628 A1 * | 4/2005 | Cazzini | A61B 90/36 606/4 |
| 2005/0171408 A1 * | 8/2005 | Parker | A61B 90/36 600/249 |
| 2008/0081952 A1 * | 4/2008 | Josephberg | A61B 17/0231 600/236 |
| 2011/0144641 A1 * | 6/2011 | Dimalanta, Jr. | A61F 9/00736 606/45 |

OTHER PUBLICATIONS

European Search Report for 19175168.4 dated Nov. 26, 2019.

* cited by examiner

LIGHT INSTRUMENT FOR ILLUMINATING THE INTRAOCULAR SPACE

TECHNICAL FIELD

The present invention relates to a device for an ophthalmological illumination system comprising a light instrument for illuminating the intraocular space of a human or animal eye according to Claim 1. The present invention further relates to an ophthalmological illumination system comprising such a device according to Claim 13 and to a method for the production of a device for an ophthalmological illumination system comprising a light instrument for illuminating the intraocular space of a human or animal eye according to claim 15.

PRIOR ART

The physiological structure of the eye means that the peripheral regions of the retina are not visible through a surgical microscope. Even when using additional wide-angle optics, the aperture angle of the optics used in the surgical microscope is too small. In order nevertheless to be able to operate in the peripheral regions, the corresponding region must lie in the user's field of view, wherein the user must reach exactly this region simultaneously with instruments. For this surgical situation a number of possibilities are known from the prior art. In this regard, there is the so-called 4-port technique, wherein illumination is effected by way of a light instrument fixed in the eye and depressing or buckling or indentation is carried out by means of a sclera depressor. What is disadvantageous about this technique is the use of a cost-intensive light instrument and the additional injury to the patient's eye on account of the fourth access into the eye. The sclera depressor is usually embodied in the form of a pin or in the form of a thimble, see US 2008/0081952 A1 for example. The latter likewise discloses that an illumination source such as an LED can be integrated into the sclera depressor in order to improve the illumination in the operating theatre. Another possibility is to enlist assistance from an assistant physician. In that case, firstly, illumination can be carried out by way of an endo-light instrument and, secondly, depressing or buckling can be carried out with the aid of an unilluminated auxiliary instrument by the assistant physician. However, the assistant physician must have the necessary skills for this. Furthermore, it is the case that even a very well practised team of surgeon and assistant physician does not achieve the same speed and precision as when the surgeon carries out all steps of the operation independently. In addition, the presence of an assistant physician increases the costs for the intervention.

SUMMARY OF THE INVENTION

It is an object of the present invention to overcome the disadvantages of the prior art. In particular, it is an object to specify a device for an ophthalmological illumination system which ensures safe and simple handling and at the same time good illumination.

In this regard, a device for an ophthalmological illumination system comprising a light instrument for illuminating the intraocular space of a human or animal eye is specified, wherein the device comprises a housing having a proximal housing end, a distal housing end, and an opening in the proximal housing end. The housing delimits a receptacle space, which extends in a manner proceeding from the opening in the proximal housing end along a longitudinal direction in the direction of the distal housing end. The receptacle space is configured for receiving the light instrument through the opening in the proximal housing end. The housing comprises at least one translucent material at least in the region of the distal housing end.

A translucent material is a material which is partially transmissive to light. To put it another way, the translucent material partly transmits light. To put it yet another way, the translucent material is not transparent, but rather partly transparent. A very uniform light distribution of the light emitted by the light instrument is achieved by virtue of the housing comprising at least one translucent material at least in the region of the distal housing end. This is attributable to the intrinsic properties of translucent material, which brings about a high degree of scattering and reflection of impinging light. Light reflections that disturb the user during use are avoided as a result. Owing to the fact that the light instrument is able to be received in the device, the user does not have to operate a plurality of instruments. The device thus allows safe and simple handling and at the same time ensures good illumination.

Preferably, the device consists of at least one translucent material in the region of the distal housing end. It is further preferred for the entire housing to comprise at least one translucent material, and particularly preferable to consist of at least one translucent material.

The translucent material is preferably a translucent plastic, in particular a translucent engineering plastic, preferably a translucent partly crystalline plastic, most preferably a polyoxymethylene copolymer. In addition or as an alternative thereto, it is likewise conceivable to provide the translucent material in the form of a plastic and/or a silicone having particles, preferably metal oxides such as titanium dioxide ($TiO_2$). The particles are preferably configured to scatter the light emerging from the light instrument. Said particles can thus also be referred to as scattering particles. If the translucent material is provided by a plastic having scattering particles, then the plastic can also be a transparent plastic, wherein the translucency or partial transparency of the at least distal housing end is provided by the scattering of light at the scattering particles. Conceivable transparent plastics are thermoplastics, engineering plastics or partly crystalline plastics such as are known to the person skilled in the art. In this case, it is conceivable for the device to consist of only a single translucent material or else of a mixture of two or more translucent materials at least in the region of the distal housing end, but correspondingly also in other regions or completely.

In addition or as an alternative thereto, it is preferred for the translucent material to have an absorption constant of approximately $10^{-3}$ in the visible wavelength range. It is conceivable for the absorption constant to be between approximately $1 \cdot 10^{-3}$ and $9 \cdot 10^{-3}$ in the visible wavelength range. In addition or as an alternative thereto, it is also conceivable, however, for the distal housing end to have a transmission of at least 60%, preferably of at least 70%, particularly preferably of at least 80%, in the visible wavelength range. In this respect, it should be understood that the term "transmission" is taken to mean the total transmission, the principal component of which stems from the translucent material, although additional secondary components such as the geometric configuration of the distal housing end also play a part. This aspect will be explained more thoroughly later.

Preferably, the device is configured for indenting the eye tissue, in particular the sclera. Indentation, also called depression or buckling, is a spatial displacement of the eye tissue using an auxiliary instrument. As a result of this displacement, tissue of interest reaches the field of view of the user, that is to say the surgeon. The latter can thus perform the desired interventions in the region that has been displaced in this way. Preferably, the device is thus both an illumination instrument and a so-called sclera depressor configured for indenting the sclera. To put it another way, the device is preferably an illuminated sclera depressor. This affords the advantage that light can reach the rear segment of the eye even without a trocar and thus without an access or port in the eye. Further advantages reside in the low costs, since a sclera depressor can be used without an additional illumination instrument, and since the user does not require an assistant physician. If the translucent material is provided by a partly crystalline plastic such as polyoxymethylene copolymer, then the device is additionally distinguished by good sliding properties on account of a low coefficient of friction.

The housing preferably comprises at least one first region and a second region adjacent thereto, wherein the distal housing end is arranged in the first region, wherein an external diameter of the first region is greater than an external diameter of the second region, and wherein a ratio between the external diameter of the first region and the external diameter of the second region is in particular more than 1. In addition or as an alternative thereto, it is preferred if the ratio between the external diameter of the first region and the external diameter of the second region is between 1.1 and 2.0, preferably between 1.3 and 1.7, and particularly preferably approximately 1.5. A conceivable external diameter of the first region is preferably between 2 millimetres and 8 millimetres, in particular approximately 6 millimetres. A conceivable external diameter of the second region is preferably between 0.5 millimetre and 6 millimetres, in particular between approximately 1 millimetre and 4 millimetres.

In other words, the first region, or distal region, of the housing has a larger external diameter than the second region adjacent thereto, or the second region is made thinner in relation to the first region. This ensures that there is enough space between the outer surfaces of the eye such as the tissue and the eye sockets such as the cranial bones, the musculature, the wall of the eye, the adipose tissue, etc., and possible further instruments such as a lid retractor, for example, which imparts freedom of movement to the device and allows the device to move on the surface of the eye in a simple manner during the depressing.

Preferably, the distal housing end is configured substantially in calotte-shaped or has the shape of a sphere substantially flattened at least on one side. In addition or as an alternative thereto, it is preferred if the distal housing end defines, in relation to the longitudinal direction an aperture angle for emerging light of the light instrument of greater than 100°, preferably of approximately 110°, in accordance with EN-ISO 15752:2010. In addition or as an alternative thereto, it is preferred if the housing defines, in the region of the distal housing end, a canonical solid angle which is 2·π (pi) steradian, wherein said solid angle forms a lateral surface of a right circular cone having a half, planar aperture angle of 90°, such that within said solid angle α radiant intensity of the light of the light instrument emerging from the region of the distal housing end is at least 30%, preferably at least 60%, most preferably at least 90%, of the radiant intensity of the light of the light instrument within said solid angle. This configuration results in a small decrease in the power of the light over a large angular range.

As has already been mentioned in the introduction, the device is distinguished by a very low loss of light, which firstly is made possible by the translucent material itself. Secondly, the sphere or calotte shape results in the light being reflected to some other spatial location. In other words, the combination of translucent material and a sphere or calotte shape brings about a homogenization of the emerging light, radiant intensity of the emerging light being lost substantially solely on account of the (low) absorption of the translucent material. The sphere flattened on one side has the effect that a width of the sphere, or to put it another way the thickness of the sphere, can be increased. This affords the advantage that shallower angles are formed between the eye tissue and the sphere surface of the distal housing end, which in turn results in a lower movement resistance and correspondingly less wrinkling. Moreover, a larger region of the eye tissue can be depressed, as a result of which the intervention can be carried out more rapidly and more distant regions of the eye tissue can be reached.

A configuration in the shape of a calotte or in the shape of a sphere affords the advantage that the distal end region comprises rounded edges and at the same time no slots or other unevennesses. The risk of injury to the conjunctiva and wrinkling are reduced or even prevented as a result. Furthermore, these configurations result in a substantially symmetrical radiation of light from the device. The user can therefore concentrate on the depressing or the actual steps of the operation and need not be concerned with the alignment of the device. Moreover, these configurations result in a lower movement resistance.

Preferably, the housing comprises a third region, wherein the proximal housing end is arranged in the third region, and wherein the third region, proceeding from the proximal housing end as viewed in the direction of the distal housing end, is configured in a manner tapering inwards at least partly in the direction of the longitudinal direction.

In other words, it is preferred for the housing to comprise a first or distal region having the shape of a calotte or the shape of a sphere flattened at least on one side, a second or central region adjacent thereto and having a smaller external diameter compared with the first or distal region, and also a conically tapering third or proximal region adjacent to said second or central region. Preferably, the second region is configured in a substantially cylindrical fashion and is configured such that it is longer than the first and third regions in relation to the longitudinal direction. The second region can be regarded as an elongate shaft. The receptacle space preferably extends completely through the third region and also the second region and at least partly into the first region.

It is preferred for a clear width of the receptacle space proceeding from the proximal housing end as viewed in the direction of the distal housing end to decrease preferably substantially continuously. By virtue of this internal diameter of the housing that becomes larger proceeding from the distal housing end as viewed in the direction of the proximal housing end, the flexural strength of said housing additionally increases. Furthermore, a ratio between the external diameter of the second or central region and an internal diameter of said second or central region is preferably greater than 1, in particular greater than 1.1.

Preferably, the housing has a wall thickness of approximately 0.5 mm to 3 mm, in particular of approximately 1.5 mm, in the region of the distal housing end in relation to a transverse direction running perpendicularly to the longitudinal direction. In addition or as an alternative thereto, the housing has a wall thickness of approximately 0.5 mm to 3 mm, in particular of approximately 1 mm, in the region of the distal housing end as viewed along the longitudinal direction.

In other words, the housing is configured with a small material thickness at least in the region of the distal housing end, that is to say in the first or distal region. The small material thickness reduces light losses as a result of absorption and results in an increase in the light power radiated from the device.

Preferably, the housing has a roughness of approximately 0.2 to 2.2 Ra in accordance with EN ISO 1302, preferably of approximately 0.4 to 2 Ra in accordance with EN ISO 1302, particularly preferably of approximately 0.6 to 0.8 Ra in accordance with EN ISO 1302, on an outer side at least in the region of the distal housing end. Preferably, the second region and/or the third region of the housing have/has on their/its outer side in each case the same roughnesses as the first region or the region of the distal housing end. Alternatively, it is also conceivable to provide these regions having different roughnesses.

Preferably, the device is releasably connectable to the light instrument, wherein the housing is configured in particular for forming a positively locking and/or force-locking connection to the light instrument. The device can be a disposable article that is removed from the light instrument after use and is disposed of. In the case of a new intervention, a new device can be connected to the light instrument. Multiple use of the light instrument is possible as a result.

Furthermore, it is conceivable to choose the dimensioning of the third or proximal region of the housing in such a way that it substantially corresponds to the dimensioning of the light instrument in the region of the connection to the device. In this context, substantially identical dimensions means that the third region of the housing defines an internal diameter which is slightly larger than an external diameter of the light instrument in the region of the connection to the device. Slightly larger in turn means that the region to be connected of the light instrument is able to be received substantially without play in the proximal or third region of the housing. This type of configuration allows a secure and at the same time simple connection, the device being pushed onto the light instrument, for example.

Preferably, the device is configured such that it is completely closed with the exception of the opening in the proximal housing end. To put it another way, the housing completely surrounds the light instrument received therein, as a result of which the light instrument is protected against contamination. This therefore also allows simple and safe multiple use of the light instrument. In other words, during an intervention on the same patient, the device can be removed temporarily from the light instrument and be fitted to the light instrument again at a later point in time. The device can thus be used repeatedly during the same intervention.

Preferably, the housing has at least one reinforcing rib in the region of the proximal housing end on an inner side facing the receptacle space. Particularly preferably, a plurality of reinforcing ribs are present, each extending parallel to the longitudinal direction. The reinforcing ribs increase the flexural strength of the device. Furthermore, it is advantageous if a respective interspace is formed between the reinforcing ribs, and correspondingly formed projections on the light instrument are able to be received into said interspace. In this case, the reinforcing ribs enable positively locking anti-torsion protection vis-à-vis undesired torsion of the device relative to the light instrument. Unintentional release of the device from the light instrument can thereby be prevented.

In a further aspect, an ophthalmological illumination system comprising a device as described above and a light instrument is specified, wherein the light instrument preferably comprises a light guide for guiding light, for example a light beam. The light guide is preferably a fibre.

It should be understood that all statements made above in respect of the device are analogously applicable to the device in the case of the ophthalmological illumination system.

The light guide is mounted in the receptacle space of the device in such a way that a ratio between i) a distance between a distal end of the light guide and a centre of the distal housing end, in particular the centre of the distal housing end substantially in the shape of a calotte or of the distal housing end in the shape of the sphere substantially flattened at least on one side, and ii) the external diameter of the first region of the housing, in particular the external diameter in the region of the centre of the distal housing end substantially in the shape of a calotte or of the distal housing end in the shape of the sphere substantially flattened at least on one side, is less than 1.5. In addition or as an alternative thereto, the distal end of the light guide is preferably arranged in the centre of the distal housing end substantially in the shape of a calotte or of the distal housing end in the shape of the sphere substantially flattened at least on one side. Centre here is understood to mean that location within the receptacle space at which the distal housing end has its maximum extent or the largest external diameter in relation to a transverse direction running perpendicularly to the longitudinal direction.

This configuration or arrangement in combination with the homogeneously scattering material has the effect that light reflections are expanded and the luminance decreases. Reflections that may disturb the user during use can thus be avoided. Specifically, by virtue of there being a spacing between the distal end of the light guide and the distal housing end, the distal or first region of the device is not completely surrounded by the eye tissue. Accordingly, light is not absorbed or is only partly absorbed by the tissue.

In a further aspect, a method for the production of a device for an ophthalmological illumination system comprising a light instrument, in particular of a device as described above, for illuminating the intraocular space of a human or animal eye is specified, wherein the method comprises the step of: injection moulding a housing having a proximal housing end, a distal housing end and an opening in the proximal housing end using an injection-moulding tool, wherein a receptacle space is formed in the housing, said receptacle space extending in a manner proceeding from the opening in the proximal housing end along a longitudinal direction in the direction of the distal housing end, and wherein at least one translucent material is used at least for the region of the distal housing end.

BRIEF DESCRIPTION OF THE DRAWINGS

Preferred embodiments of the invention are described below with reference to the drawings, which serve merely for elucidation and should not be interpreted as restrictive. In the drawings:

FIG. 10b shows a side view of the light instrument in accordance with FIG. 10a;

FIG. 10c shows a partial sectional view of the light instrument in accordance with FIG. 10a;

FIG. 10d shows a further perspective view of the light instrument in accordance with FIG. 10a;

FIG. 11b shows a side view of the light instrument in accordance with FIG. 11a;

FIG. 11c shows a partial sectional view through the light instrument in accordance with FIG. 11a;

FIG. 13b shows measurements of the normalized radiant intensity in [%] of the light instrument in accordance with FIG. 13a in a second orientation in relation to the aperture angles in polar coordinates, said second orientation being rotated by 90 degrees in relation to the orientation shown in FIG. 13a;

DESCRIPTION OF PREFERRED EMBODIMENTS

Various aspects of an ophthalmological illumination system 1 comprising a light instrument 3 and also a device 2 for illuminating the intraocular space of a human or animal eye 33 will be discussed in association with FIGS. 1 to 16.

Figure 1:
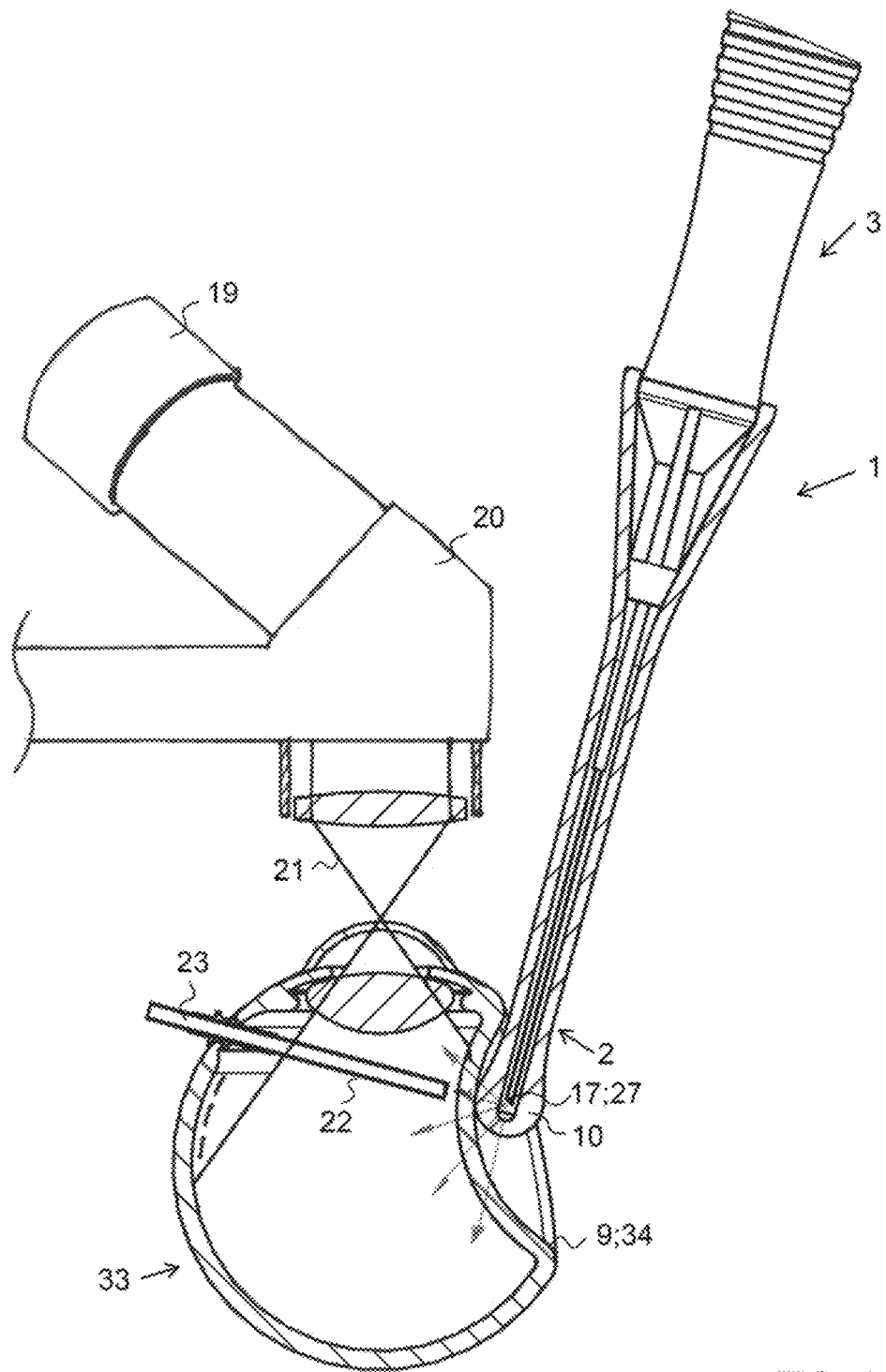
FIG. 1 shows a partial sectional view of an ophthalmological illumination system comprising a light instrument and a device in accordance with a first embodiment during a surgical application.

As is evident from FIG. 1, in particular, the device 2 serves a dual function. Specifically, firstly, the device 2 is configured for indenting the eye tissue 34, in particular the sclera 9. In other words, the device 2 is a so-called sclera depressor, by means of which the eye tissue 34 can be spatially displaced. As a result of this displacement, the tissue of interest reaches the field of view of the user, generally of the surgeon, such that the latter can perform a desired intervention in this region. In other words, the device 2 allows the visualization of peripheral regions of the eye such as the retina and the vitreous humour in order to be able to carry out surgical interventions in said regions. Secondly, the device 2 also serves for illumination. In this regard, the device is connected to the light instrument 3 of the illumination system 1, wherein light from the light instrument 3 radiates into the interior of the eye via the device 2. The device 2 can thus be referred to as an illuminated depressor or as an illuminated sclera depressor, which enables transscleral illumination of the peripherally located regions of the globe of the eye (eyeball). As will be explained even more thoroughly later, the light in this case emerges at the distal end 17 of the light instrument 3 and transmits through a distal region 10 of the sclera depressor 2 through the depressed eye tissue 34 into the interior of the eye. As indicated in FIG. 1, the user can observe the operation in this case through the eyepiece 19 of a surgical microscope 20, said user's field of view being represented by the beam path 21 in FIG. 1. Regions which do not lie in the user's field of view are forced into the field of view by the spatial displacement by means of the sclera depressor 2 according to the invention. Since the spatial displacement and the illumination are carried out with the same device 2 and with only one hand, the user is left with a free hand, which he/she can use to operate other instruments such as e.g. a vitrectome 22 for removing the vitreous humour, said vitrectome being guided through a trocar 23 into the interior of the eye.

Figure 2:
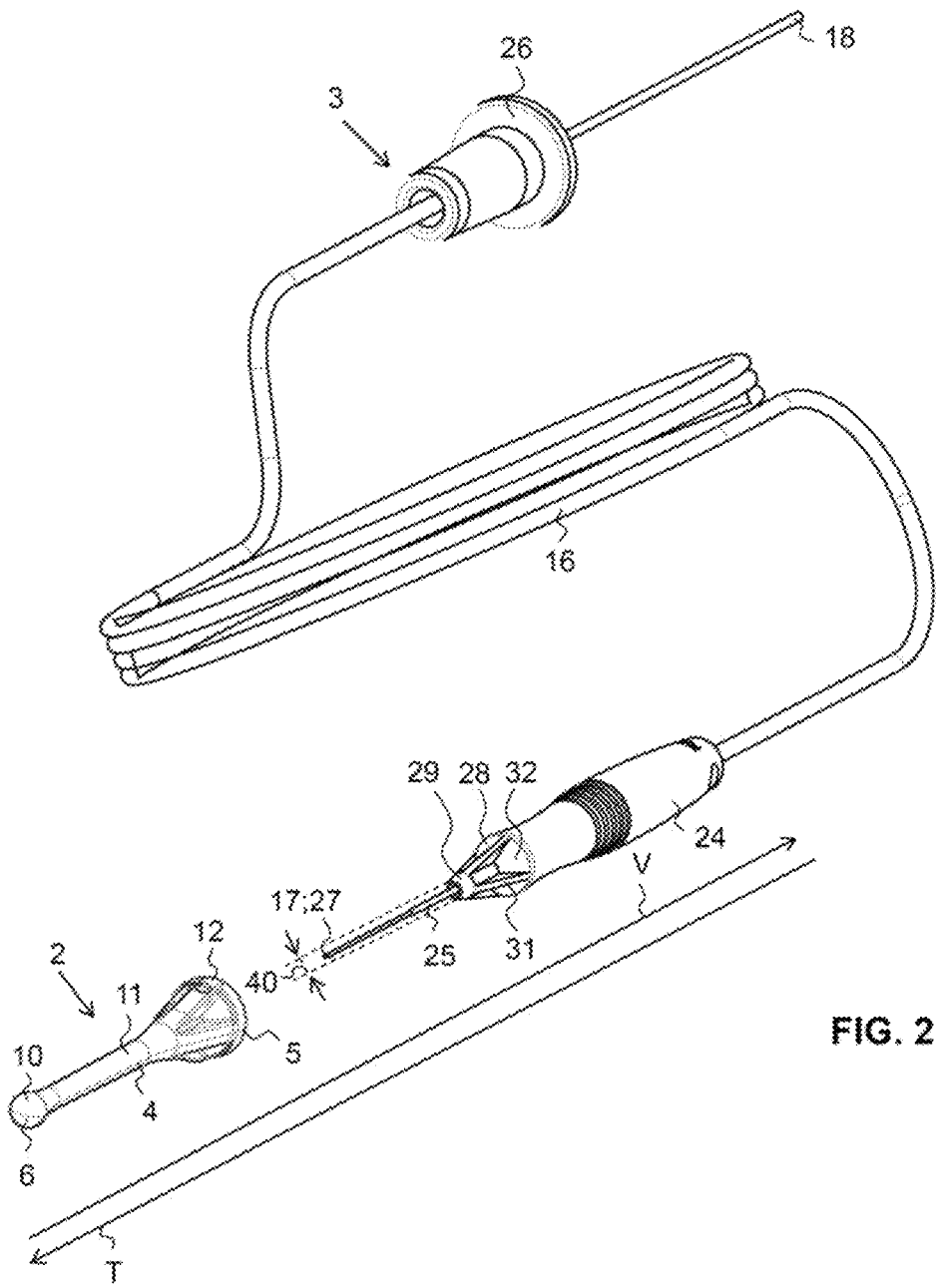
FIG. 2 shows a perspective view of the ophthalmological illumination system in accordance with FIG. 1, wherein the device is separated from the light instrument.
Figure 3:
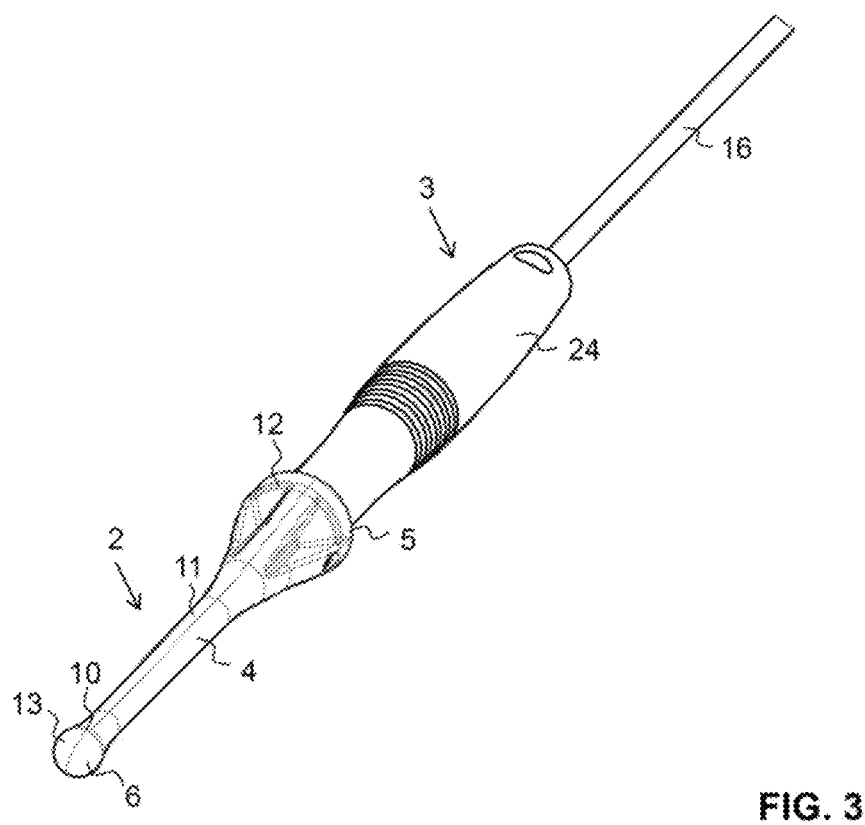
FIG. 3 shows a perspective view of the ophthalmological illumination system in accordance with FIG. 1, wherein the device is connected to the light instrument.

As is readily apparent in FIG. 2, the ophthalmological illumination system 1 comprises, together with the sclera depressor 2 and the light instrument 3, a light source (not illustrated) with a socket. In the embodiment shown, the light instrument 3 in turn comprises a handle 24, a light guide 16, a cannula 25 and a connector 26. The light guide 16 is made available here in the form of a fibre and has a proximal end 18 for coupling in light from the light source and also a distal end 17 for emitting the light coupled in. The light guide 16 is fixedly connected to the connector 26 of the light instrument 3 and light is coupled into the light guide 16 by way of the light source. Furthermore, the cannula 25 is secured to the handle 24 and the light guide 16 is connected to the handle 24 and the cannula 25. In this case, the light guide 16 extends through the handle 24 and the cannula 25 through to the distal end 27 of the cannula 25. The distal end 17 of the light guide 16 is thus situated in the region of the distal end 27 of the cannula 25, wherein light can be coupled out from the light guide 16. It is evident from FIGS. 3 to 6, in particular, that the sclera depressor 2 comprises a housing 4 having a proximal housing end 5, a distal housing end 6, and an opening 7 in the proximal housing end 5. The housing 4 delimits a receptacle space 8, which extends in the manner proceeding from the opening 7 in the proximal housing end 5 along a longitudinal direction L in the direction of the distal housing end 6. The light instrument 3, to be precise the cannula 25 and the light guide 16 mounted therein, are received into the receptacle space 8 of the sclera depressor 2 through the opening 7 in the proximal housing end 5. In the received state, the distal end 27 of the cannula 25 and hence the distal end 17 of the light guide 16 become located in the region of the distal housing end 6. By virtue of the fact that the housing 4 comprises at least one translucent material at least in the region of the distal housing end 6, light proceeding from the distal end 17 of the light guide 16 is emitted via the distal end 27 of the cannula 25 and through the distal housing end 6.

The sclera depressor 2 is releasably connectable to the light instrument 3, in particular to a distal region 28 of the handle 24. To that end, the proximal region 12 of the housing 4 and the distal region 28 of the handle 24 are configured as it were complementarily to one another. In particular, the proximal region 12 of the housing 4, proceeding from the proximal housing end 5 as viewed in the direction of the distal housing end 6, is configured in a manner tapering conically inwards in the direction of the longitudinal direction L of the sclera depressor 2. The distal region 28 of the handle 24 is also configured in a manner tapering conically inwards as viewed in the direction of the distal end 29 of the handle 24, wherein the dimensions of the conically tapering regions 12, 28 are chosen in such a way that a positively locking engagement between the conically tapering regions 12, 28 is formed when the distal region 28 of the handle 24 is received in the proximal region 12 of the sclera depressor 2. In order to connect the handle 24 to the sclera depressor 2, the sclera depressor 2 can be pushed onto the distal region 28 of the handle 24 along a connection direction V. In order to release the sclera depressor 2 from the handle 24, the user pulls the sclera depressor 2 away from the distal region 28 of the handle 24 along a separating direction T running oppositely to the connection direction V. By virtue of this type of connection, the sclera depressor 2 does not have to be held fixedly during an intervention.

Figure 4:
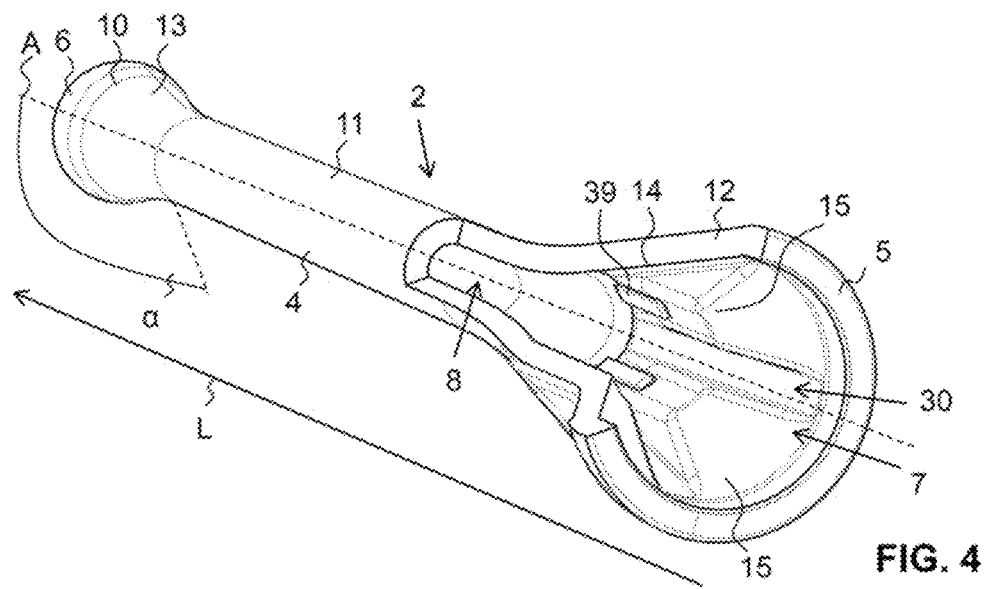
FIG. 4 shows a partial sectional view through the device in accordance with FIG. 1.
Figure 9:
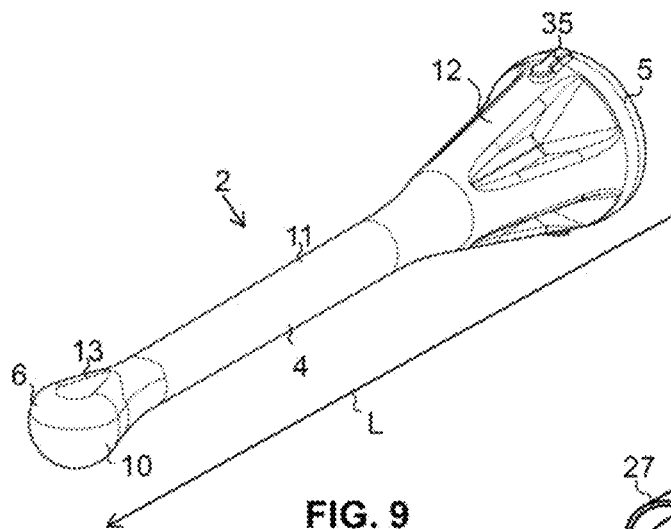
FIG. 9 shows a perspective view of a device in accordance with a third embodiment.
Figure 10A:
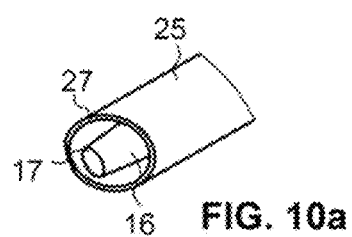
FIG. 10a shows a partial perspective view of the light instrument in accordance with the first embodiment.
Figure 10B:
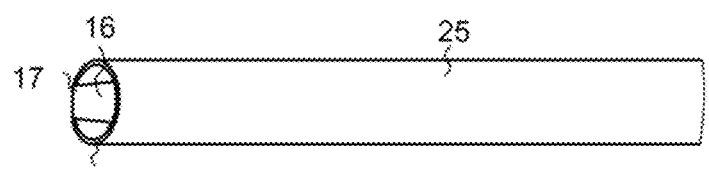
Figure 10C:
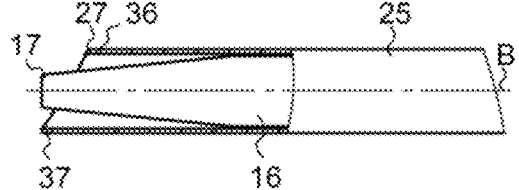
Figure 10D:
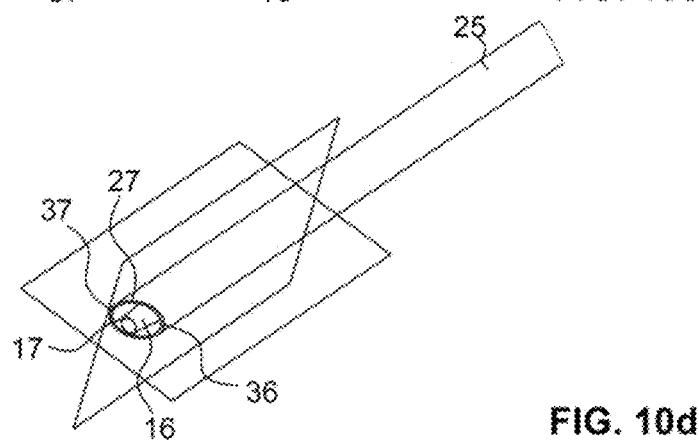
Figure 11A:
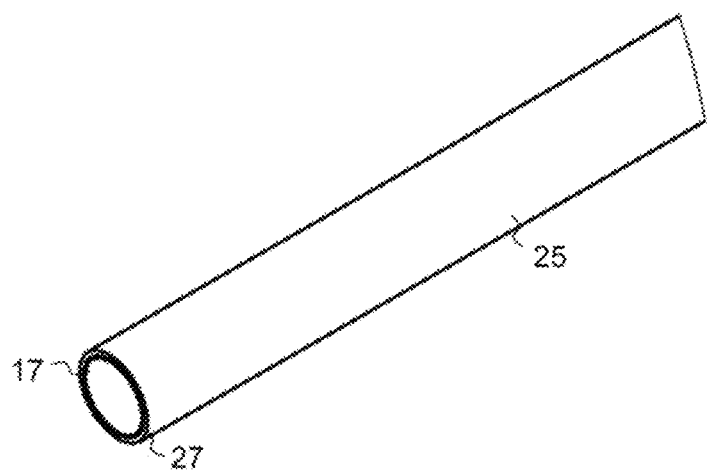
FIG. 11a shows a partial perspective view of the light instrument in accordance with a second embodiment.
Figure 11B:
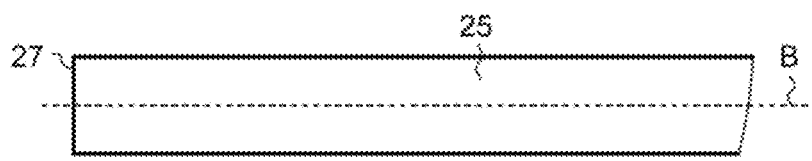
Figure 11C:
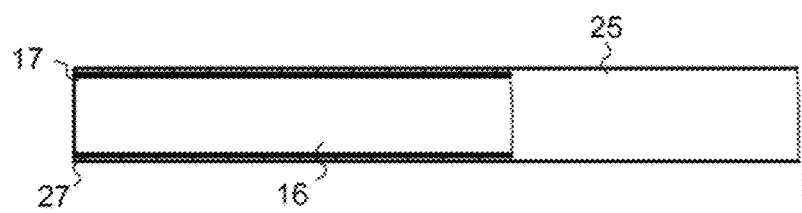
Figure 12:
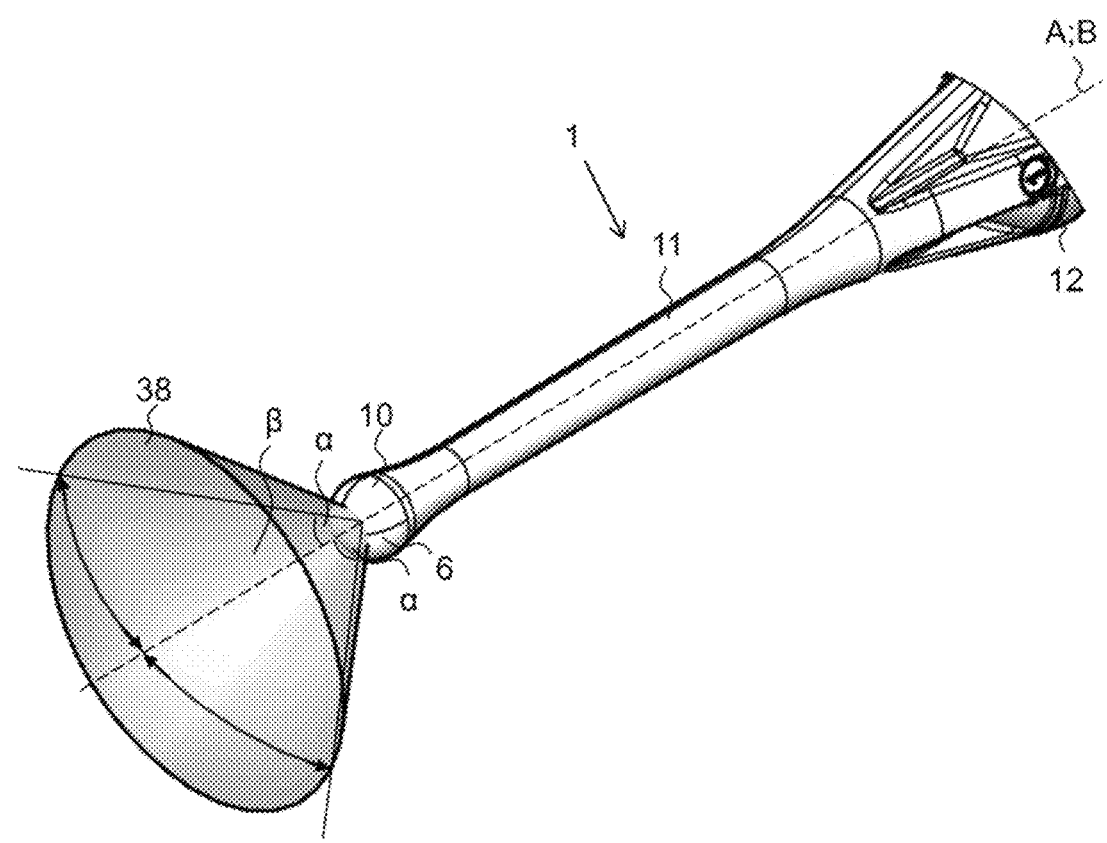
FIG. 12 shows a schematic partial view of the device in accordance with the first embodiment and the radiation characteristic thereof illustrated by a solid angle and the half, planar aperture angle thereof.
Figure 13A:
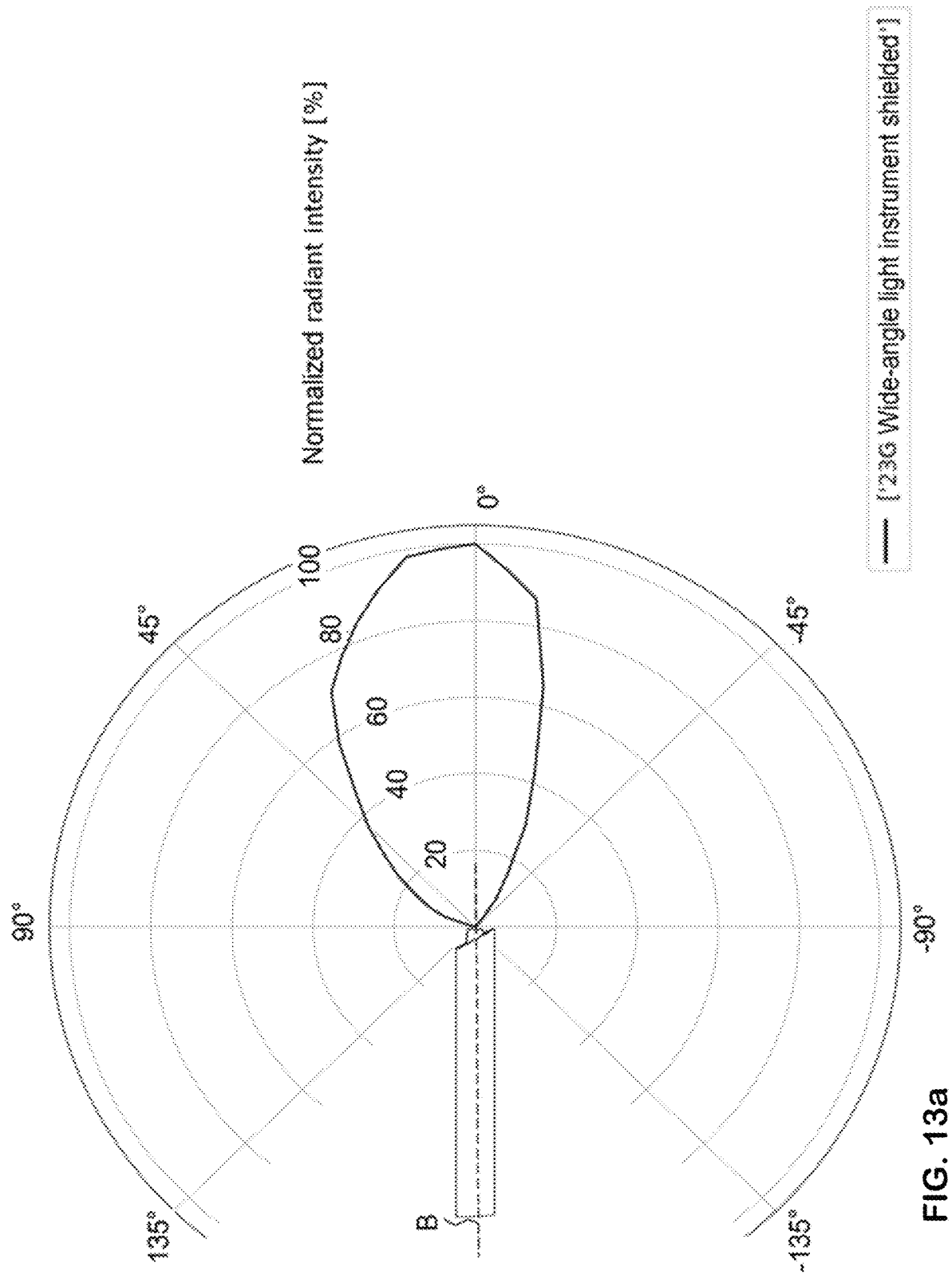
FIG. 13a shows measurements of the normalized radiant intensity in [%] of a light instrument in accordance with the first embodiment in a first orientation in relation to the aperture angles in polar coordinates.
Figure 13B:
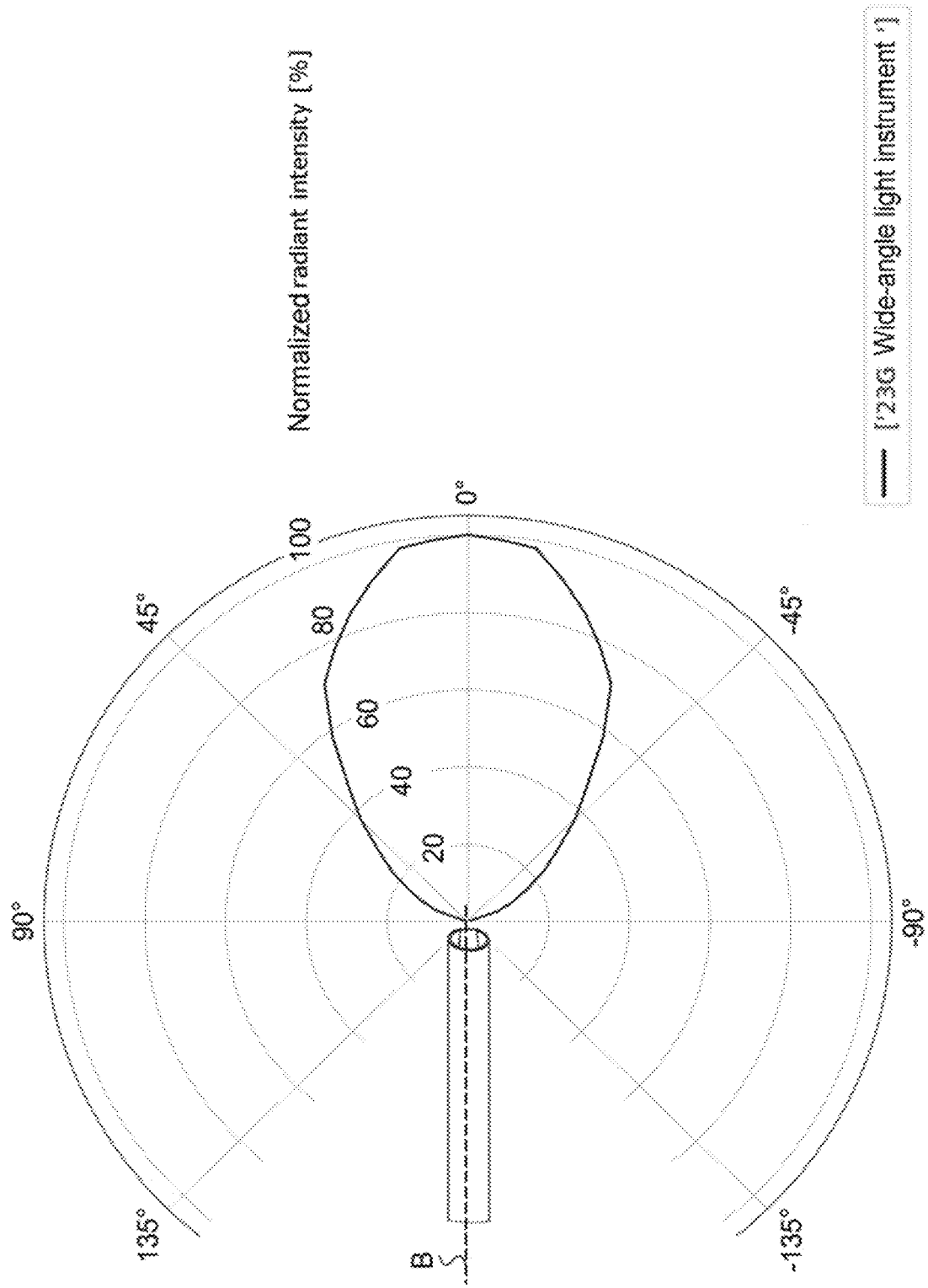

It is readily apparent in FIGS. 2 and 4 that the housing 4 of the sclera depressor 2 has a plurality of reinforcing ribs 15 in the region 12 of the proximal housing end 5 on an inner side 14 facing the receptacle space 8. In this case, the reinforcing ribs 15 extend from the inner side 14 of the housing 4 facing the receptacle space 8 parallel to the longitudinal direction L and also at least partly into the receptacle space 8. The reinforcing ribs 15 serve to increase the flexural strength of the sclera depressor 2. As is evident from FIG. 4, a respective interspace 30 is formed between two adjacent reinforcing ribs 15. Corresponding projections 31 arranged on an outer side 32 in the distal region 28 of the handle 24 are received in said interspaces 30, see FIG. 2. A further positively locking engagement and also an anti-torsion safeguard vis-à-vis a torsion of the sclera depressor 2 relative to the handle 24 and thus relative to the cannula 25 and the light guide 16 mounted therein are provided as a result. As is furthermore evident from FIG. 4, the housing 4 of the sclera depressor 2 additionally comprises ribs 39 extending along the longitudinal direction L in the region of the proximal housing end 5 on the inner side 14 of said housing. Said ribs 39 limit an internal diameter of the housing 4 substantially to an external diameter 40 of the handle 24 (see FIG. 2), such that a force-locking engagement is formed between the housing 4 at the location of the ribs 39 and the handle 24 at the location of the housing 4 in the case where a depressor 2 is connected to the handle 24. In the exemplary embodiment of the device in the form of the sclera depressor 2 as shown in FIG. 9, a tactile marking 35 is additionally situated in the region 12 of the proximal housing end 5 on an outer side 13, said tactile marking being configured as an elevation and enabling an intuitive orientation of the sclera depressor 2 for the user. This is advantageous in particular for a sclera depressor having the shape of a sphere flattened on one side, see FIG. 8.

Preferably, the sclera depressor 2 is a disposable article that is disposed of after a surgical intervention. In the present examples, the sclera depressor 2 is configured as completely closed with the exception of the opening 7 in the proximal housing end 5. In other words, apart from said opening 7, the sclera depressor 2 has no further openings. The cannula 25 received in the receptacle space 8 of the housing 4 and also the light guide 16 mounted in said cannula are protected against external influences by the housing 4 of the sclera depressor 2. Simple and safe multiple use of the light instrument 3 during the same operation is ensured as a result. By way of example, the user can firstly use the light instrument 3 with the sclera depressor 2 according to the invention, the light guide 16 and the cannula 25 being received in the receptacle space 8 of the sclera depressor 2 and being completely enveloped by the housing 4 of the sclera depressor 2. The user can then withdraw the cannula 25 and the light guide 16 mounted therein from the receptacle space 8 of the sclera depressor 2 and insert them into a trocar 23, for example, wherein the cannula 25 and the light guide 16 mounted therein are used for endo-illumination in the interior of the eye.

Figure 5A:
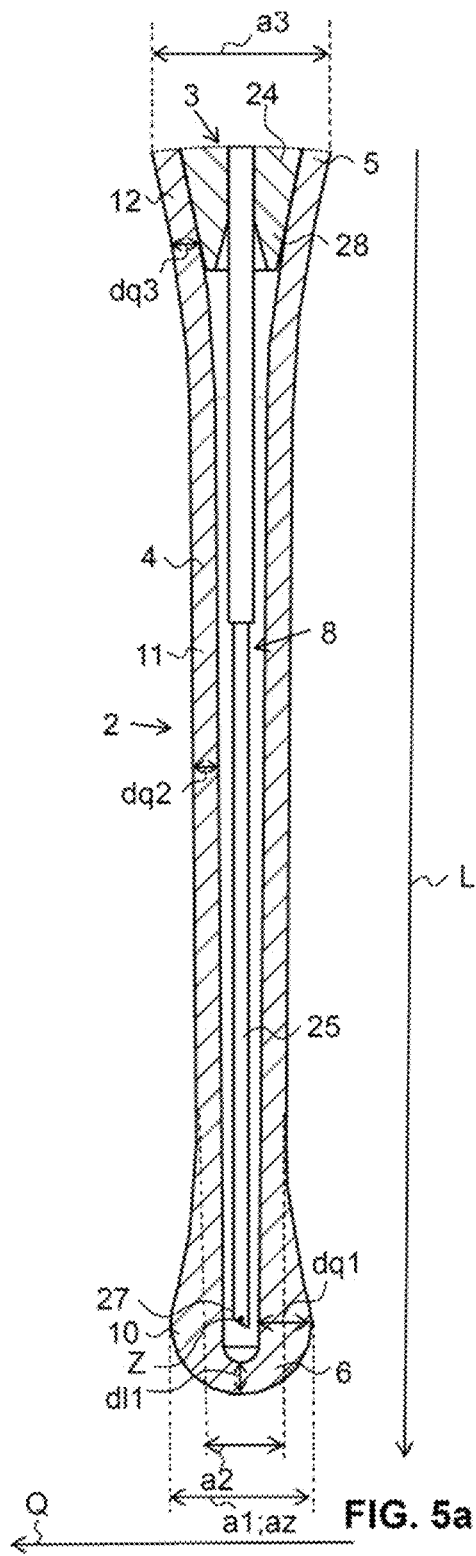
FIG. 5a shows a central longitudinal section through the device and a part of the light instrument in accordance with FIG. 1 with the light instrument at a first position.
Figure 6:
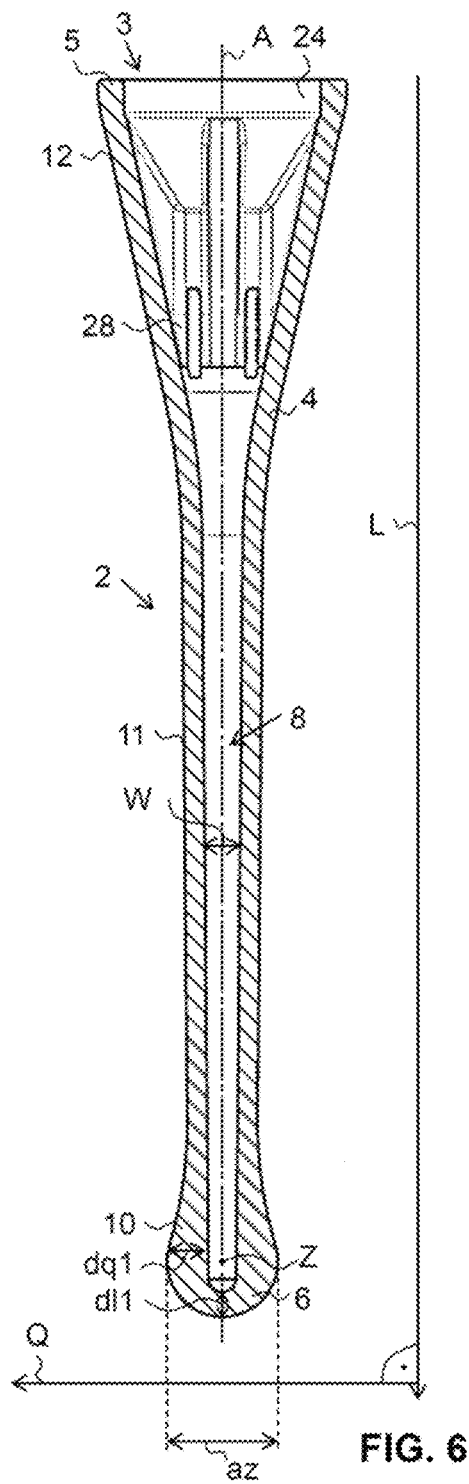
FIG. 6 shows a further central longitudinal section through the device in accordance with FIG. 1.
Figure 5B:
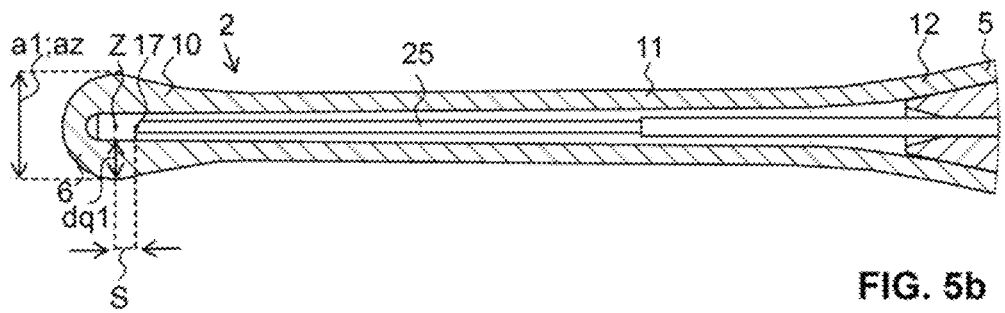
FIG. 5b shows a central longitudinal section through the device and a part of the light instrument in accordance with FIG. 1 with the light instrument at a second position.
Figure 7:
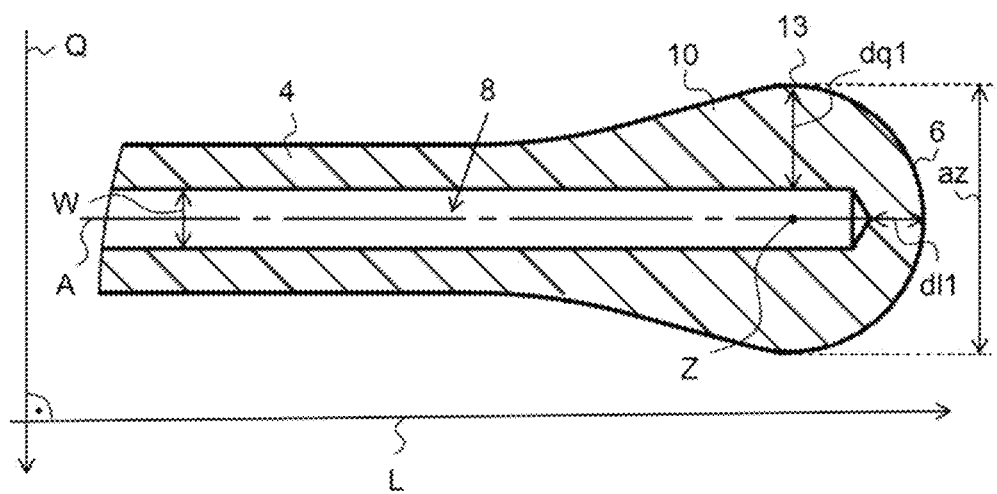
FIG. 7 shows a further central longitudinal section through a part of the device in accordance with FIG. 1.
Figure 8:
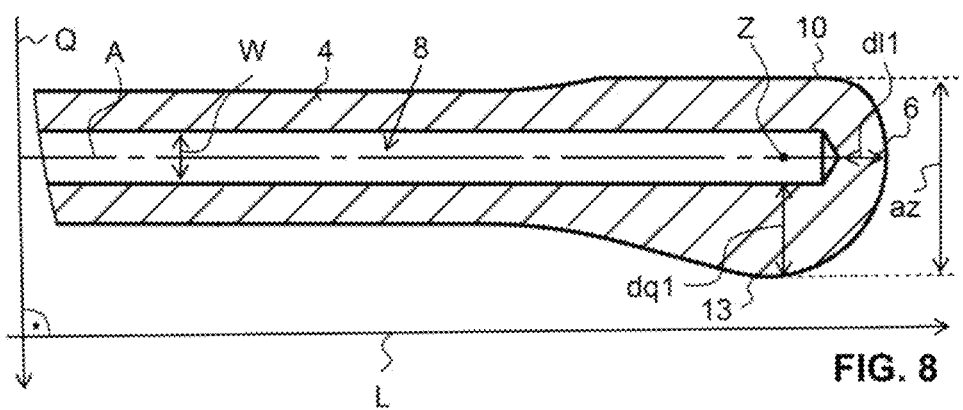
FIG. 8 shows a further central longitudinal section through a part of a device in accordance with a second embodiment.

As is evident from FIGS. 5a, 5b and 6, for example, the housing 4 of the sclera depressor 2 has an elongate shape, wherein the regions of the proximal housing end 12 and of the distal housing end 10 in each case have a larger external diameter a1, a3 by comparison with the central region 11 formed between these end regions 10, 12. To put it another way, the housing 4 comprises a first region 10 and a second region 11 adjacent thereto, wherein the distal housing end 6 is arranged in the first region 10, and wherein an external diameter a1 of the first region 10 is greater than an external diameter a2 of the second region 11. Furthermore, a ratio between the external diameter a1 of the first region 10 and the external diameter a2 of the second region 11 is more than 1, here approximately 1.5. Various embodiments for the distal region 10 of the housing 4 are conceivable here. As is shown in FIGS. 5 to 7 and 8, the distal region 10 of the housing 4 can be configured substantially in the shape of a calotte or can have the shape of a sphere substantially flattened on one side. The central region or second region 11 adjacent thereto can be configured substantially in the shape of a cylinder and can be referred to as a shaft. As already mentioned earlier, the region 12 adjacent to the central region or second region 11, that is to say the third region 12 comprising the proximal housing end 5, is configured in a manner tapering conically inwards proceeding from the proximal housing end 5 as viewed in the direction of the distal housing end 6. In this case, an external diameter a3 of the third region 12 at the location of the proximal housing end 5 is greater than an external diameter a3 of the third region 12 at a location adjoining the second region 11. Moreover, the external diameter a3 of the third region 12 at the location of the proximal housing end 5 is greater than an external diameter a1 of the first region 10 at the location of the distal housing end 6.

As is evident from FIGS. 5a and 5b, the light instrument 3, here its cannula 25 with the light guide 16 mounted therein, is received in the receptacle space 8 of the device 2 in such a way that the distal end 17 of the light guide 16 becomes located in the centre Z or in the vicinity of the centre Z of the distal housing end 6 in the shape of a sphere or calotte. Centre Z is understood here to be that location within the receptacle space 8 at which the distal housing end 6 has its maximum extent or the largest external diameter az in relation to a transverse direction Q running perpendicularly to the longitudinal direction L. Specifically, a ratio between i) a distance S between the distal end 27 of the cannula 25 and the centre Z and ii) the external diameter az of the distal region 10 of the housing 4 in the region of the centre Z of the distal housing end substantially in the shape of a calotte or of the distal housing end in the shape of the sphere substantially flattened at least on one side is less than 1.5. In the case shown in FIG. 5a, the distal end 27 of the cannula 25, and hence the distal end 17 of the light guide 16 mounted in the cannula 25, is situated in the centre Z. In the case shown in FIG. 5b, the distal end 27 of the cannula 25, and hence the distal end 17 of the light guide 16 mounted in the cannula, is at a distance S from the centre Z. In the specific example, said distance S is approximately 0.5 mm, other distances also being conceivable, of course. These configurations or arrangements in combination with the homogeneously scattering material of the depressor 2 have the effect that light reflections are expanded and the luminance decreases. Light reflections that disturb the user during use can be avoided as a result. The disturbing reflections arise in the region of the sclera depressor 2 in which the distal end 27 of the cannula 25 is situated, that is to say in the first region or the distal region 10. The light being transmitted from the light instrument 3 is reflected at the inner interface of the housing 4 and reaches the user's eye. Since the distal end 27 of the cannula 25 in the case of the sclera depressor 2 according to the invention does not lie at the distal housing end 6, but rather in the centre Z or in the vicinity of the centre Z of the first region or of the distal region 10, this part of the sclera depressor 2 is not continuously completely surrounded by the eye tissue and the light is thus not absorbed or is only partly absorbed by the tissue.

A loss of light intensity is further prevented by the choice of the wall thicknesses dl1, dq1 of the sclera depressor 2 in the regions in which the light has to transmit through the housing 4 of the sclera depressor 2. In this regard, it is preferred to form the distal region 10 of the housing 4 with a small material thickness, as a result of which light losses are reduced on account of absorption of the material. By way of example, the housing 4 can have a wall thickness dq1 of approximately 0.5 mm to 3 mm, in particular of approximately 1.5 mm, in the region 10 of the distal housing end 6 in relation to a transverse direction Q running perpendicularly to the longitudinal direction L, and/or the housing 4 can have a wall thickness dl1 of approximately 0.5 mm to 3 mm, in particular of approximately 1 mm, in the region 10 of the distal housing end 6 as viewed along the longitudinal direction L.

As is readily apparent in FIGS. 5 and 6, the wall thickness dq2, dq3 in the second and third regions 11, 12, as viewed along the transverse direction Q, remains constant in each case and is of approximately the same magnitude in the second region 11 as in the third region 13. However, the clear width W of the receptacle space 8 decreases substantially continuously proceeding from the proximal housing end 5 as viewed in the direction of the distal housing end 6. One reason for this resides in the manufacturing technique. In this regard, the core has to be "released from the mould", which necessitates a uniform angle. In the injection-moulding method, in the case of such demanding component parts, a constant wall thickness is an almost mandatory basic prerequisite. Furthermore, the flexural strength increases as a result of the internal diameter, that is to say the clear width W, becoming larger and larger.

The sclera depressor 2 according to the invention, in particular an outer side 13 in the region 10 of the distal housing end 6, is preferably provided with a roughness of approximately 0.2 to 2.2 Ra in accordance with EN ISO 1302, preferably of approximately 0.4 to 2 Ra in accordance with EN ISO 1302, particularly preferably of approximately 0.6 to 0.8 Ra in accordance with EN ISO 1302. This roughness is crucially influenced in particular by the production process during the production of the device in the injection-moulding method by virtue of milling and eroding processes. In addition to the favourable sliding properties of the translucent material, such a surface roughness enables very simple movement of the sclera depressor 2 on the globe of the eye (eyeball), without the eye tissue adhering to the sclera depressor 2.

Various aspects of the light instrument 3, in particular of the cannula 25 thereof and the light guide 16, will be discussed in association with FIGS. 10a to 10d and 11a to 11c. The radiation characteristics resulting therefrom will be explained with reference to FIGS. 12 to 16b. As is evident from a comparison of FIGS. 10a to 10c and 11a to 11d, the cannula 25 and the light guide 16 mounted therein differ in terms of the distal ends 17 and 27 thereof. Specifically, the cannula 25 and the light guide 16 in accordance with FIGS. 10a to 10d in each case exhibit a conically ground light guide 16 and an obliquely ground cannula 25, which is in contrast to the light guide 16 ground in planar fashion and the cannula 25 ground in planar fashion in accordance with FIGS. 11a to 11c. Light instruments 3 comprising a cannula 25 and a light guide 16 having distal ends 27, 17 ground in planar fashion in each case are referred to as "90° light instruments", while light instruments 3 comprising a cannula 25 and a light guide 16 having an obliquely ground and a conically ground distal end 27, 17, respectively, are referred to as "wide-angle light instruments". The oblique ground face of the cannula 25 in the case of the wide-angle light instrument has the effect that the distal end 27 of the cannula 25 has a shortened and a lengthened cannula region in relation to a central longitudinal axis B running centrally through the cannula 25. The lengthened region can also be referred to as a shielded region which, in the case of regular devices from the prior art, is directed towards the user in order to protect the latter against glare from the light.

The geometric configuration of the distal end 10 of the housing 4 together with the translucent material from which the distal region 10 of the housing 4 is formed have the effect that the distal region 10 of the housing 4 radiates the light approximately like a diffuse spherical emitter. This in turn has the effect that a uniform illumination of the depressed eye tissue 34 is achieved, specifically independently of the light instrument 3 used. This will now be shown on the basis of measurement examples.

In particular, the measurement examples in each case show the radiation characteristic of 90° light instruments 3 and of wide-angle light instruments 3 with and without the use of the sclera depressor 2 according to the invention. The radiation characteristic is illustrated in each case on the basis of the aperture angle α of a canonical solid angle D. In other words, and as is evident from schematic FIG. 12, the device or the sclera depressor 2, through the distal housing end 6 thereof, radiates light 38 from the light instrument 3 mounted therein. In this case, the geometric configuration and the constitution of the distal housing end 6 are such that the housing 4 defines, in the region of the distal housing end 6, a canonical solid angle β which is 2·π steradian, wherein said solid angle β forms a lateral surface of a right circular cone having a half, planar aperture angle α of 90 degrees. The measurements shown in the figures show in each case the radiant intensity for various aperture angles α in relation to the central longitudinal axis B through the light instrument 3 (FIGS. 13a to 14) and respectively in relation to the central longitudinal axis A through the device or the sclera depressor 2 (FIGS. 15a to 16b).

Figure 14:
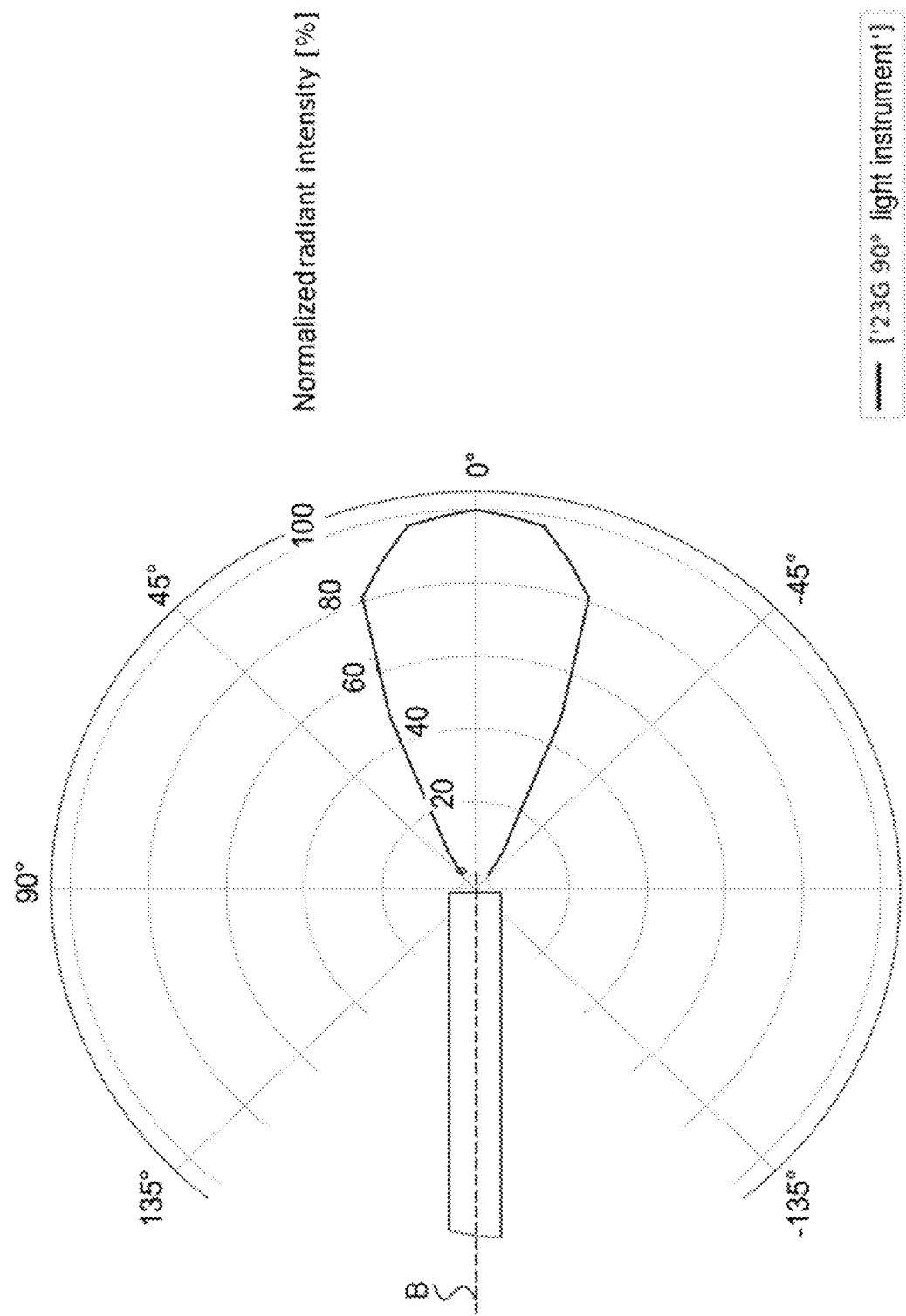
FIG. 14 shows measurements of the normalized radiant intensity in [%] of a light instrument in accordance with the second embodiment in relation to the aperture angles in polar coordinates.
Figure 15A:
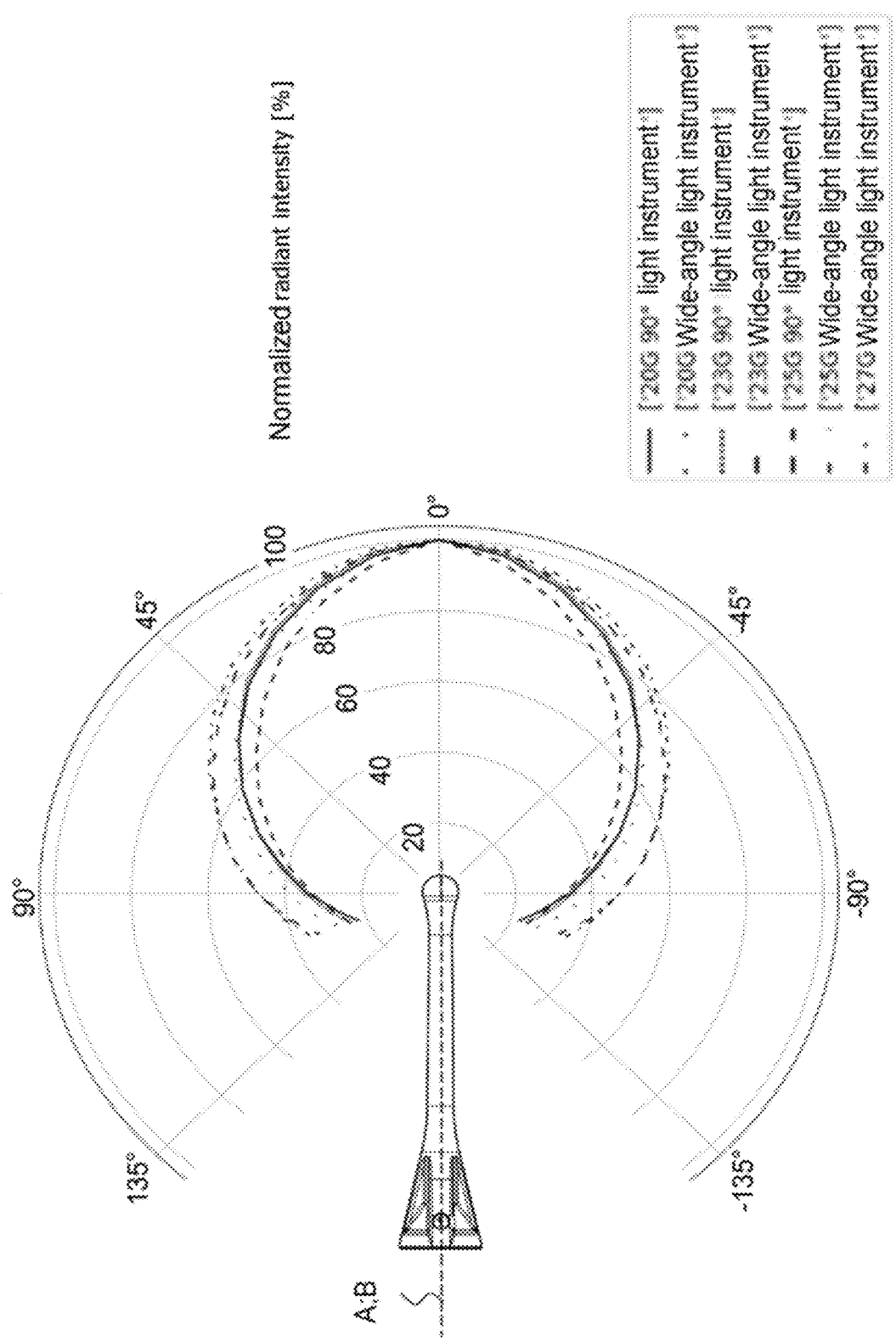
FIG. 15a shows measurements of the normalized radiant intensity in [%] of a device in accordance with the first embodiment with a first wall thickness with different types of light instruments in accordance with the first and second embodiments in relation to the aperture angles in polar coordinates.
Figure 15B:
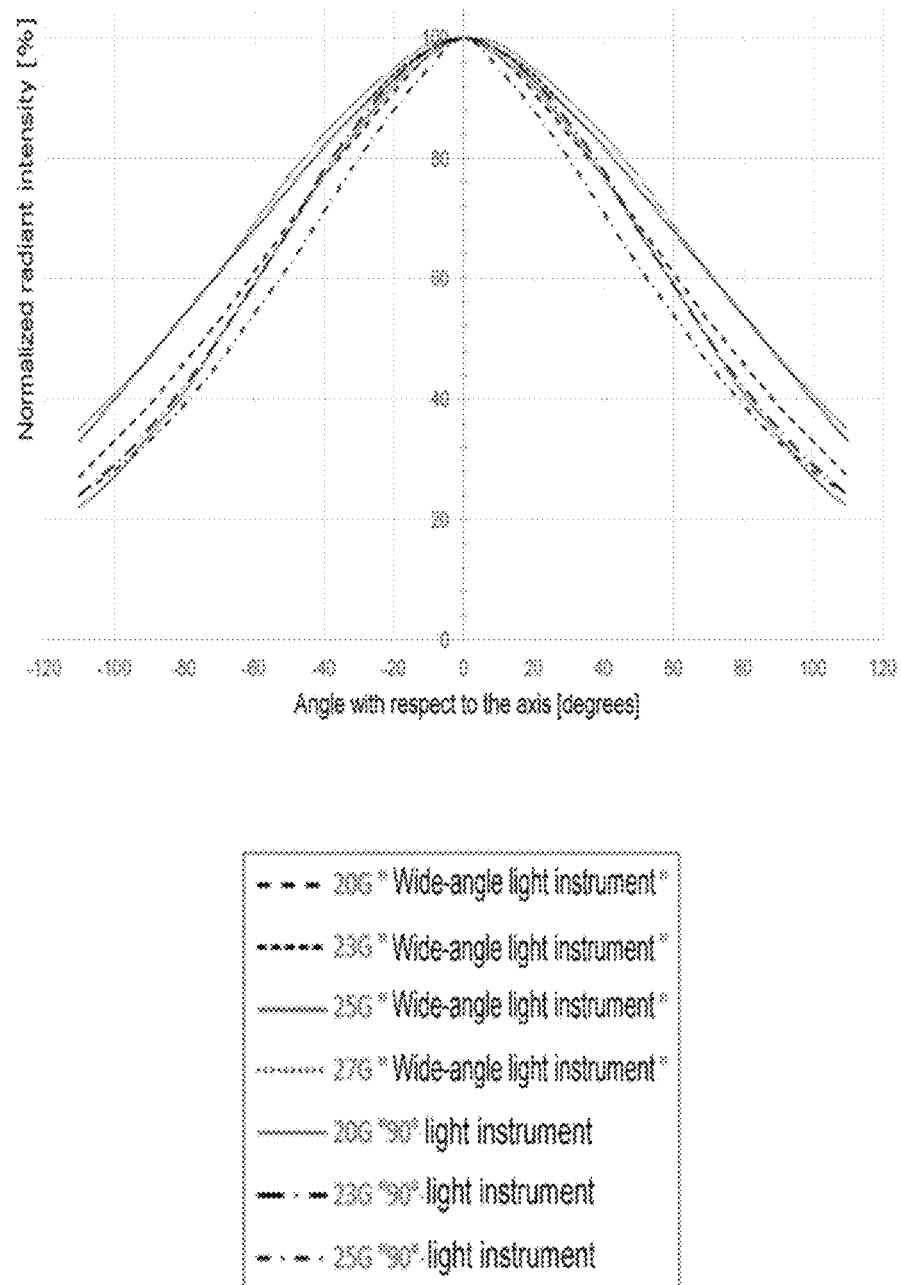
FIG. 15b shows the measurements of the normalized radiant intensity in [%] in relation to the aperture angles of the device and the different types of light instruments in accordance with FIG. 15a in Cartesian coordinates.

As is evident from FIG. 14, a 90° light instrument has a symmetrical radiant intensity in relation to its central longitudinal axis B. The same also applies to the wide-angle light instrument if the light power measurement is carried out at the shortened region 36 of the cannula, see FIG. 13b. In the case of a light power measurement at the lengthened or shielded region of the cannula 37, the profile of the light power is asymmetrical on account of the region of the cannula that forms the shield, see FIG. 13a. As is then evident from a comparison of FIGS. 13a to 14 with FIGS. 15a to 16b, the sclera depressor 2 according to the invention is able to compensate for the asymmetry of the light power for a light instrument 3 comprising a cannula 25 and a light guide 16 having an obliquely ground and a conically ground distal end 27, 17, respectively. The sclera depressor according to the invention thus results as it were in light beam expansion.

Figure 16A:
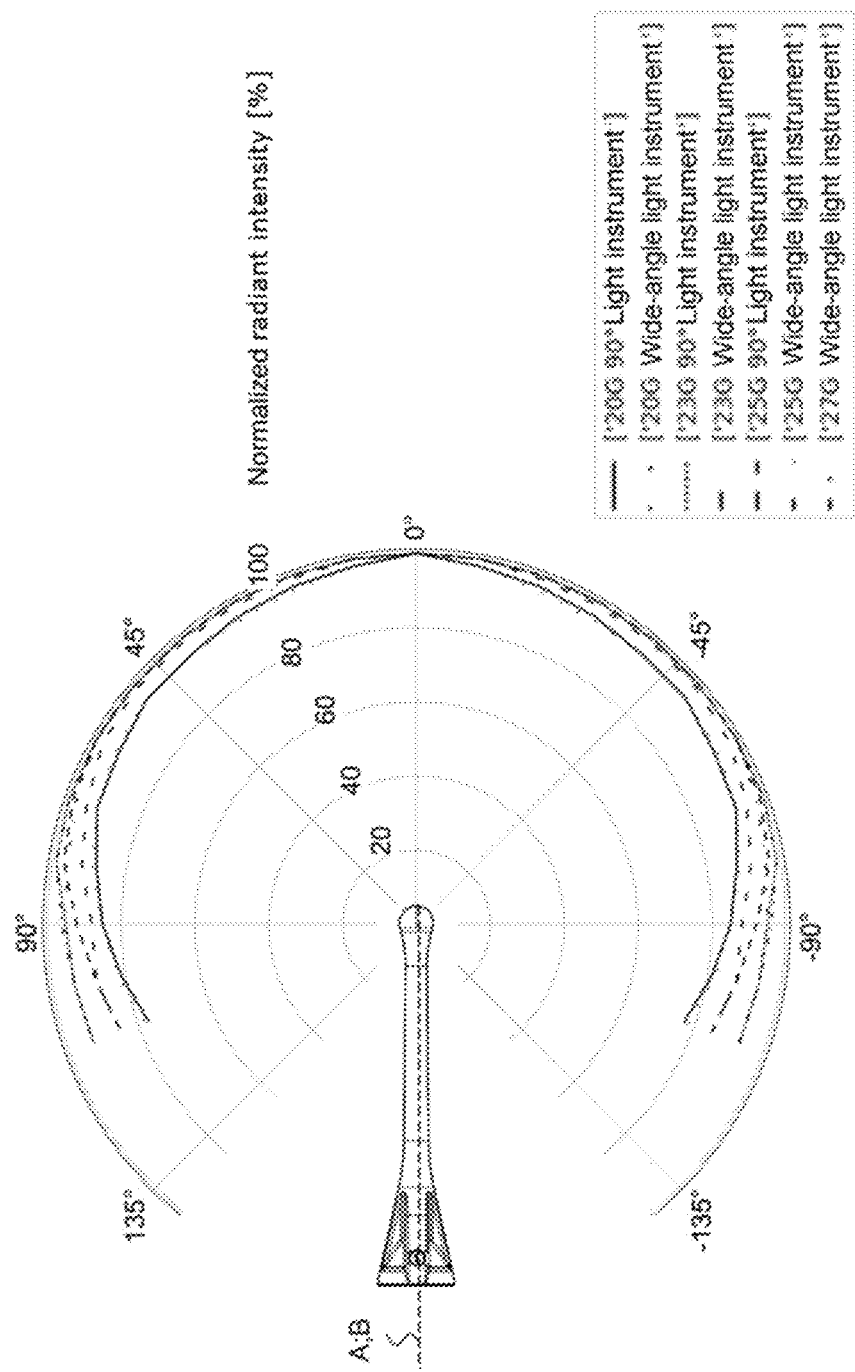
FIG. 16a shows measurements of the normalized radiant intensity in [%] of a device in accordance with the first embodiment with a second wall thickness with different types of light instruments in accordance with the first and second embodiments in relation to the aperture angles in polar coordinates.
Figure 16B:
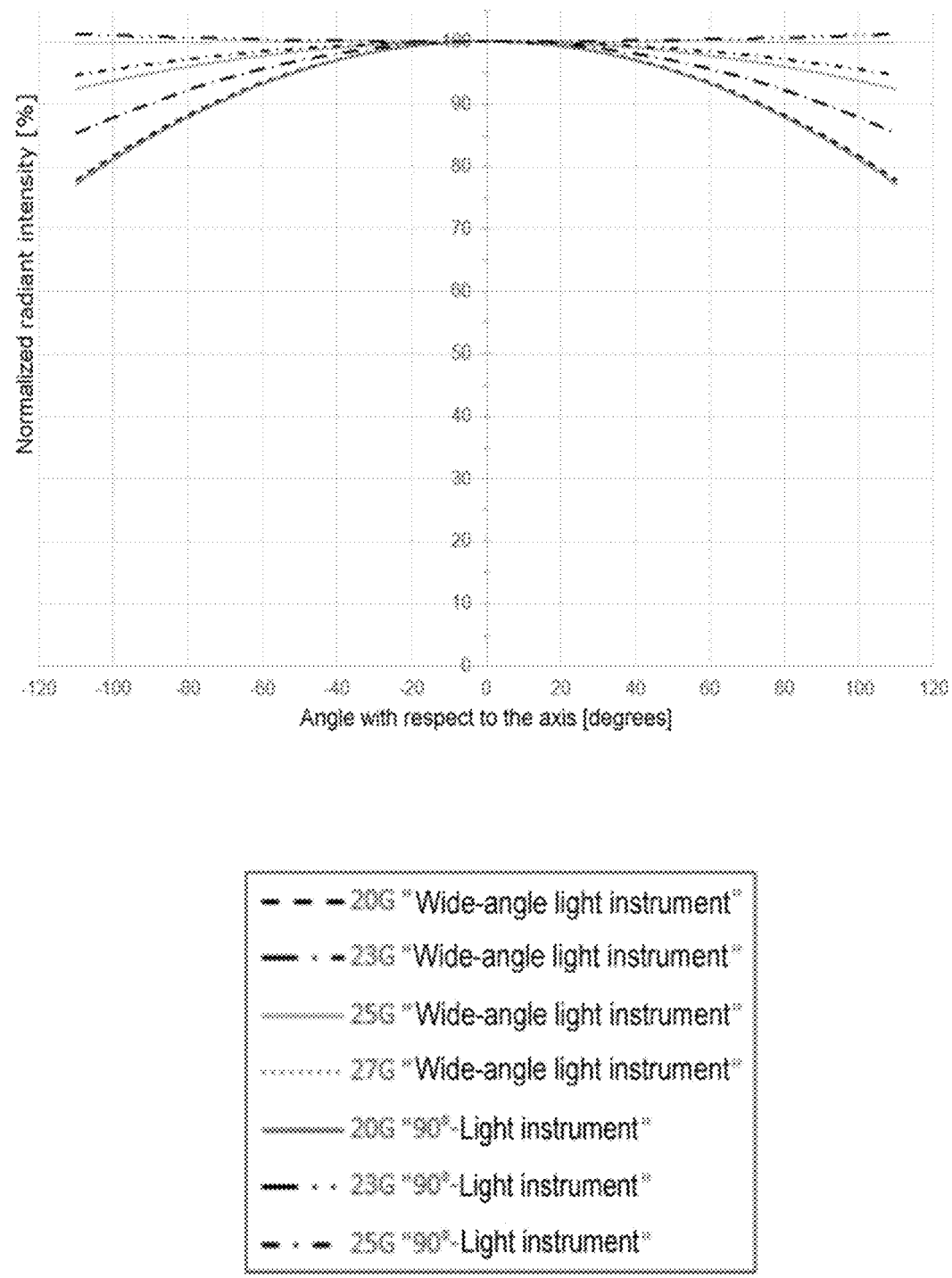
FIG. 16b shows the measurements of the normalized radiant intensity in [%] in relation to the aperture angles of the device and the different types of light instruments in accordance with FIG. 16a in Cartesian coordinates.

In other words, and as is evident from FIGS. 15a to 16b, the radiation characteristic of the sclera depressor 2 according to the invention is such that a deviation of the light power between the so-called 90° light instrument and the so-called wide-angle light instrument, for various types of light instrument, is approximately 20% or less. As is evident from the legends in FIGS. 15a to 16b, said various types of light instrument are the 20G, 23G, 25G and 27G types known to the person skilled in the art, wherein "G" stands for gauge. The device 2 or the sclera depressor which was used for the measurements in FIGS. 15a to 16b differs in each case in its wall thickness. In other words, the sclera depressor in accordance with FIGS. 15a and 15b comprises a housing 4 having a wall thickness dl1 of approximately 0.8 millimetre in the region of the distal housing end as viewed along the longitudinal direction L, while the wall thickness dl1 of the sclera depressor in accordance with FIGS. 16a and 16b is approximately 2.2 millimetres. In both cases, the sclera depressor has a distal end region in the shape of a calotte. As is additionally evident from FIGS. 15a to 16b, a radiant intensity over a large angular range is furthermore achieved with the sclera depressor 2 according to the invention. In particular, the sclera depressor 2 according to the invention allows emission of light through its distal region 10 of the housing 4 with a radiant intensity of approximately 20% or more for the sclera depressor in accordance with FIGS. 15a and 15b (wall thickness dl1 of approximately 0.8 millimetre) and respectively of approximately 80% or more for the sclera depressor 2 in accordance with FIGS. 16a and 16b (wall thickness dl1 of approximately 2.2 millimetres) for an aperture angle α of greater than 100°. By virtue of the fact that the sclera depressor 2 has a very uniform radiation characteristic, there is the further advantage that the permissible treatment time can be considerably increased without phototoxic reactions arising in the tissue of the eye.

The invention claimed is:

1. A device for an ophthalmological illumination system comprising a light instrument for illuminating the intraocular space of a human or animal eye,
    wherein the device comprises a housing having a proximal housing end a distal housing end, and an opening in the proximal housing end,
    wherein the housing delimits a receptacle space, which extends in a manner proceeding from the opening in the proximal housing end along a longitudinal direction in the direction of the distal housing end,
    wherein the receptacle space is configured for receiving the light instrument through the opening in the proximal housing end,
    wherein the housing comprises at least one translucent material at least in the region of the distal housing end,
    wherein the device is configured for indenting the eye tissue,
    wherein the distal housing end defines, in relation to a central longitudinal axis of the housing, an aperture angle for emerging light of the light instrument of approximately 110° in accordance with EN-ISO 15752: 2010,
    wherein at least one of:
       a) the distal housing end is configured substantially in the shape of a calotte or has the shape of a sphere substantially flattened at least on one side, and
       b) the housing defines, in the region of the distal housing end, a canonical solid angle which is 2·π steradian, and
    wherein said solid angle forms a lateral surface of a right circular cone having a half, planar aperture angle of 90 degrees, such that within said solid angle a radiant intensity of the light of the light instrument emerging from the region of the distal housing end is at least 60% of a radiant intensity of the light of the light instrument within said solid angle.

2. The device according to claim 1, wherein at least one of:
    a) the translucent material is a translucent plastic, and
    b) the translucent material is at least one of i) a plastic and ii) a silicone having particles, wherein the particles are configured to scatter impinging light emitted by the light instrument, and
    c) the translucent material has an absorption constant of approximately 10^(−3) in the visible wavelength range.

3. The device according to claim 2, wherein the translucent material is a translucent engineering plastic or a translucent partly crystalline plastic or a polyoxymethylene copolymer.

4. The device according to claim 1,
    wherein the housing comprises at least one first region and a second region adjacent thereto,
    wherein the distal housing end is arranged in the first region, and
    wherein an external diameter of the first region is greater than an external diameter of the second region.

5. The device according to claim 4, wherein at least one of a ratio between the external diameter of the first region and the external diameter of the second region is more than 1, and the ratio between the external diameter of the first region and the external diameter of the second region is between 1.1 and 2.0.

6. The device according to claim 1,
wherein the housing comprises a third region, wherein the proximal housing end is arranged in the third region, and
wherein the third region, proceeding from the proximal housing end as viewed in the direction of the distal housing end, is configured in a manner tapering inwards at least partly in the direction of the longitudinal direction.

7. The device according to claim 1, wherein a clear width of the receptacle space proceeding from the proximal housing end as viewed in the direction of the distal housing end decreases.

8. The device according to claim 7, wherein the clear width of the receptacle space proceeding from the proximal housing end as viewed in the direction of the distal housing end decreases substantially continuously.

9. The device according to claim 1, wherein at least one of:
a) the housing has a wall thickness of approximately 0.5 mm to 3 mm in the region of the distal housing end in relation to a transverse direction running perpendicularly to the longitudinal direction, and
b) the housing has a wall thickness of approximately 0.5 mm to 3 mm in the region of the distal housing end as viewed along the longitudinal direction.

10. The device according to claim 1, wherein the housing has a roughness of approximately 0.2 to 2.2 Ra in accordance with EN ISO 1302 on an outer side at least in the region of the distal housing end.

11. The device according to claim 1, wherein the device is releasably connectable to the light instrument.

12. The device according to claim 11, wherein the housing is configured for forming at least one of a positively locking and force-locking connection to the light instrument.

13. The device according to claim 1, wherein the device is configured such that it is completely closed with the exception of the opening in the proximal housing end.

14. The device according to claim 1, wherein the housing has at least one reinforcing rib in the region of the proximal housing end on an inner side facing the receptacle space.

15. An ophthalmological illumination system comprising a device according to claim 1 and a light instrument.

16. The ophthalmological illumination system according to claim 15, wherein at least one of:
a) the light instrument is mounted in the receptacle space of the device in such a way that a ratio between:
i. a distance between a distal end of the light instrument and a centre of the distal housing end, and
ii. the external diameter of the first region of the housing is less than 1.5, and
b) the distal end of the light instrument is arranged in the centre of the distal housing end substantially in the shape of a calotte or of the distal housing end in the shape of the sphere substantially flattened at least on one side.

17. The ophthalmological illumination system according to claim 15, wherein the light instrument comprises a light guide for guiding light.

18. A method for producing a device for an ophthalmological illumination system comprising a light instrument for illuminating the intraocular space of a human or animal eye, the method comprising the step of:
injection moulding a housing having a proximal housing end, a distal housing end and an opening in the proximal housing end using an injection-moulding tool,
wherein a receptacle space is formed in the housing, said receptacle space extending in a manner proceeding from the opening in the proximal housing end along a longitudinal direction in the direction of the distal housing end,
wherein the receptacle space is configured for receiving the light instrument through the opening in the proximal housing end,
wherein at least one translucent material is used at least for the region of the distal housing end, and
wherein the device is configured for indenting the eye tissue, and
wherein the distal housing end defines, in relation to a central longitudinal axis of the housing, an aperture angle for emerging light of the light instrument of approximately 110° in accordance with EN-ISO 15752:2010,
wherein at least one of:
a) the distal housing end is configured substantially in the shape of a calotte or has the shape of a sphere substantially flattened at least on one side, and
b) the housing defines, in the region of the distal housing end, a canonical solid angle which is $2 \cdot \pi$ steradian, and
wherein said solid angle forms a lateral surface of a right circular cone having a half, planar aperture angle of 90 degrees, such that within said solid angle a radiant intensity of the light of the light instrument emerging from the region of the distal housing end is at least 60% of a radiant intensity of the light of the light instrument within said solid angle.

* * * * *